(12) United States Patent
Thurow

(10) Patent No.: US 6,328,564 B1
(45) Date of Patent: Dec. 11, 2001

(54) DEEP EAR CANAL LOCATING AND HEAD ORIENTING DEVICE

(76) Inventor: Raymond C. Thurow, 8058 Coray La., Verona, WI (US) 53593

(*) Notice: Subject to any disclaimer, the term of this patent is extended or adjusted under 35 U.S.C. 154(b) by 0 days.

(21) Appl. No.: 09/286,847

(22) Filed: Apr. 6, 1999

(51) Int. Cl.$^7$ .................................................. A61C 19/04
(52) U.S. Cl. .............................................. 433/72; 181/130
(58) Field of Search .............................. 433/72; 181/135, 181/130

(56) References Cited

U.S. PATENT DOCUMENTS

| | | | |
|---|---|---|---|
| 3,097,059 | * 7/1963 | Hoffman | 264/155 |
| 4,616,998 | * 10/1986 | Wong | 433/73 |
| 5,781,637 | * 7/1998 | Heide et al. | 381/68.6 |

* cited by examiner

Primary Examiner—John J. Wilson
Assistant Examiner—Melba Bumgarner
(74) Attorney, Agent, or Firm—Henry W. Cummings

(57) ABSTRACT

A device fitted to the external auditory canal for the purpose of reproducibly engaging the head for orientation and stabilization for dental or radiographic (commonly known as 'cephalometric') recording and for placing a radiographic marker in the canal.

28 Claims, 3 Drawing Sheets

DEEP EAR CANAL LOCATING AND HEAD ORIENTING DEVICE

FIELD OF THE INVENTION

A device fitted to the external auditory canal for the purpose of reproducibly engaging the head for orientation and stabilization for dental or radiographic (commonly known as 'cephalometric') recording and for placing a radiographic marker in the canal.

BACKGROUND OF THE INVENTION

The external ear canal has been used as a basis for dental orientation and measurement since the nineteenth century. Artificial dentures and other dental prostheses are typically fabricated in a laboratory on casts of the jaws mounted on a mechanical articulator which approximates the functional relationships of the jaws. How well the teeth on the articulator imitate natural function depends in a large part on relating them correctly to the joints that control jaw movement.

Positioning the casts of the teeth in the articulator is typically accomplished by a 'face bow transfer' which uses an adjustable rigid bow that engages the upper teeth in front and the two ear canals in back. This relies on earposts in the ear canals as the basis for estimating the actual position of the joints, and it is subject to significant error because of the anatomical characteristics of the external ear canal that is engaged by the facebow. Efforts continue today to improve the accuracy and reproducibility of these procedures.

When cephalometric radiography was developed by Broadbent in the 1920's, it was also based on ear canal orientation of the head. The external mechanism is aligned with the x-ray source through movable right and left earposts that engage the outer ear canals. Cephalometric radiographs have become a standard component of orthodontic diagnosis, and the axis connecting the ear canals or related proxy landmarks are still the underlying foundation for measurements derived from these films in all three planes of space.

The orientation of the head on the ear canal axis is controlled by engaging the outer ear canals with a rigidly mounted mechanism usually called a 'cephalostat' or 'cephalometer,' and this continues to be a major source of error in this technique. Limits of precision exist for every method of measurement, and over time they often become accepted as an integral part of the technique and either factored into measurements or ignored. That is the current state in cephalometrics. The orienting mechanism can be made to any degree of precision, but the anatomy of the engaged ear structures still provides a very poor and inconsistent engagement. Alternative methods proposed up to this time have failed to offer significant improvement.

The external auditory meatus area is irregular in shape, highly variable, mobile, and very sensitive. Those anatomical characteristics make it impossible to engage it with the consistency required for reproducible positioning and precision measurement, but it is all that we have had. The ear canals are the only bilateral structures that can be readily engaged mechanically. Earposts for engaging the canals have been fabricated in various cylindrical, conical or bulbous forms, but all suffer from the same basic problems that prevent predictable or reproducible orientations with the accuracy required for precision applications.

SHORTCOMINGS OF EARPOST ORIENTATION OF THE HEAD

The classical cephalometric engagement of the head by coordinated insertion of machine-mounted earposts into the external auditory canals is a trying one for both operator and patient. While the operator is trying to insert the two earposts uniformly to maximum depth, keeping the head perfectly oriented with the earpost axis intersecting the sagittal plane at a 90 deg. angle, the patient is responding predictably to the resulting discomfort or pain. Shifting and squirming are typical in the search for a more comfortable position for both sides. When the operator feels that the earposts are inserted as far and as uniformly as possible the instruction to, "hold still" is issued while retreating behind a barrier to make the x-ray exposure. Predictably, the two sides are rarely aligned exactly, and taking another film with the identical orientation is impossible. This becomes especially critical when the mechanism and patient must be rotated to one of more companion views oriented in different Cartesian planes.

A close look at the anatomy of the ear canal will quickly show why the many variations in earpost form and size have failed to solve the problems of accuracy and comfort. FIG. 1 shows the relevant anatomy of the external ear canal 10 and the position and general course of the canal upward and posteriorly as it progresses inward to the ear drum. These top and rear views of a full-size impression of the outer portion of the canal clearly show the irregular shape of the canal that defies consistent engagement by any standardized earpost. The outside view in FIG. 2 completes the picture. The concha 12 of the external ear collects sound and directs it toward the funnel-shaped aperture of the external acoustic meatus 16 immediately behind the tragus 18. The canal initially continues directly inward from there, and that is as far as we can usually see. It is also as far as a cephalostat earpost can initially penetrate, but the canal extends inward a long way from there. As soon as there is room for a turn, it turns sharply in a posterior 14 and slightly upward 20 direction, and then turns more inward 22 after another short run. The canal becomes smaller and more round as it continues on at about a 45 degree angle beyond the reach of the impression shown at 26 to the eardrum.

Individual canals vary widely in size and shape as they progress inward, with even wider variations among individuals. As can be seen in FIG. 1, the crosssection even in a single canal varies from nearly round 28 to flattened ovoid 30, and from large to small. The deviant course and changing cross-section of the external canal makes accurate engagement for orientation of the head with any one earpost shape an unattainable objective.

The problem is further complicated by the proximity of underlying cartilage and bone, combined with the sensitivity of the lining of the canal. The outer portions are supported only by very mobile cartilage and other soft tissues, gradually approaching rigid bone as the canal progresses inward. This increases both stability and sensitivity as we progress inward, causing patients to shift unpredicably as they search for a more comfortable position.

The above problems have always been obvious to clinicians, and they have limited the utility of cephalometric measurement to structures and applications that can tolerate the inevitable variability.

IDENTIFYING ANATOMICAL POSITION

Orienting the head is just the first of two functions of the engagement of the ear canal. The other is to provide a pair of bilateral anatomic reference points to establish a line that can serve as the basis for measurement in the horizontal, vertical and transverse Cartesian planes of space. There are no bilateral anatomical points that can be reliably identified on x-ray images in more than one plane of space, so it is necessary to rely on secondary markers. Common practice uses a radiopaque marker attached to the earpost, so the same variability described above also affects these anatomic markers.

III THE DRAWINGS

FIG. 5b is a schematic plan view of FIG. 5a.

IV DESCRIPTION OF INVENTION AND PREFERRED EMBODIMENTS

This invention is a removable precision molded ear canal implant that converts the large irregular canal opening to a socket designed to accurately receive the earpost of an external positioning device, and optionally includes an embedded radiopaque marker to provide an x-ray reference point. This greatly reduces patient discomfort while improving positioning accuracy far beyond that which can be achieved with conventional methods. The radiopaque marker further improves x-ray accuracy by providing an accurate landmark close to underlying bone and identifiable in x-ray views in all three planes of space.

Figure 1A:
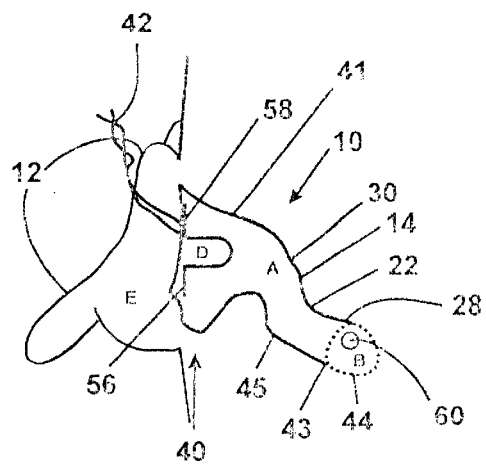
FIG. 1a is a schematic plan view of the head of a patient illustrating the auditory canal.
Figure 1B:
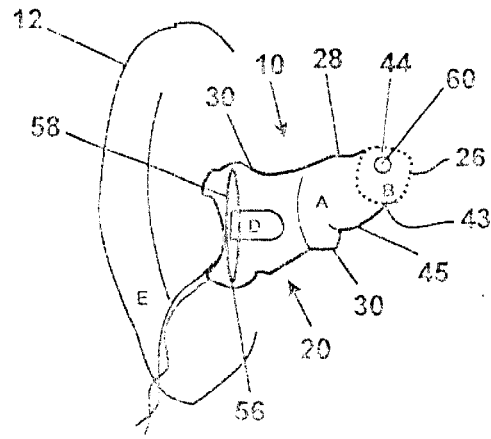
FIG. 1b is a schematic side elevation of a patient's head illustrating the auditory canal.
Figure 1C:
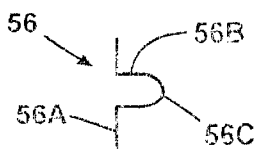
FIG. 1c is a schematic side elevation view illustrating a radiolucent socket embedded in the exposed end of the earmold shown in 1a and 1b.

This is accomplished with an innovative modified impression of the canal 40 such as the one shown in FIG. 1. The impression is made using methods and materials known to the arts of dentistiy and of hearing aid fabrication. Typical materials are commonly used two-part silicone-based impression materials which solidify to a stable suitably elastic non-shrinking product a short time after the two components are mixed and placed in the ear canal. The resulting device may then be removed from the ear canal and reinserted for subsequent procedures or used for laboratory fabrication of a reproduction in a different material. Optional fabrication of a reproduction in a different material can provide additional control over form, flexibility and durability.

These impressions 40 are typically made by first attaching a strong thread 42 to a soft canal blocker 44, such as a small cotton ball. The blocker is inserted into the ear canal, 10 to the desired depth 43 to limit the penetration of the impression material 41, while the thread 42 is left hanging outside the canal to aid in retrieval of the impression. The impression material 41 is then mixed, placed in a syringe and injected into the canal. After the material has solidified, the impression 40 is removed with the aid of the protruding thread.

Figure 2:
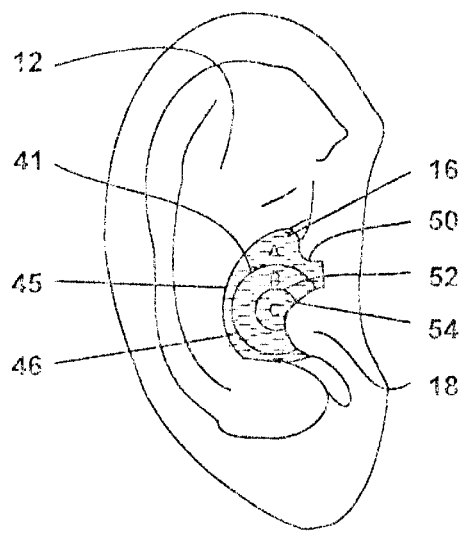
FIG. 2 is a schematic side elevation view of the right ear illustrating an earmold impression with a socket insert.
Figure 5A:
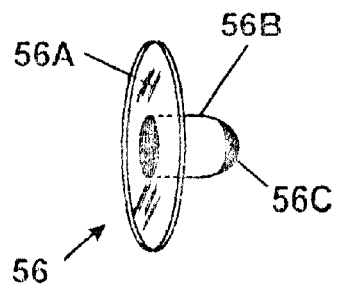
FIG. 5a is a schematic perspective view of a radiolucent socket for embedment in the lateral face of the earmold.
Figure 5B:
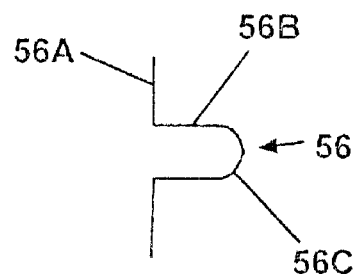
Figure 5C:
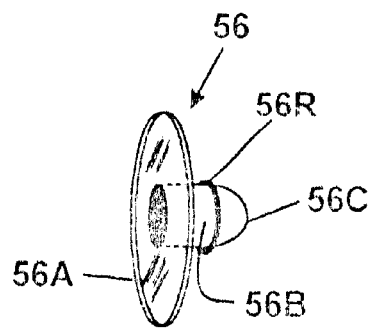
FIG. 5c is a schematic perspective view illustrating an annular projection ring which may be incorporated to further secure the socket in the earmold.

A locator device 50 is made by modifying the impression 40 described above in one or more, of the following ways (FIGS. 1, 2, 5).

1. A removable form 52 resembling an earpost is inserted into the soft impression material 41 immediately after the soft material is placed in the ear. Removing this form after the material 41 has solidified leaves a socket 54 for the insertion of the earpost.

A disadvantage of this method is the softness of the socket, which is easily damaged and will allow some movement. Method 2, below, mitigates those disadvantages.

2. A rigid radiolucent socket 56 is securely embedded in the external face 58 of the impression before the material solidifies. This socket typically embodies a flange 56a to resist displacement by the pressure of earpost insertion, a hollow cylindrical or hemispherical body portion 56b to receive the earpost, a closed tip 56c and optional ring(s) 56r or other external projections to enhance retention in the earmold. This provides a sturdier socket for accurate reproducible placement of the earpost.

The modifications 1&2 described above provide a major advance in positioning accuracy for cephalometric radiography and for dental facebow mounting techniques. However, additional enhancement is required to provide a clearly identifiable radiopaque landmark for x-ray applications. The current practice of using a radiopaque attachment to the earposts may be used, but this is not as reliably located in all x-ray views, is subject to variations in earpost insertion and is supported mostly by mobile soft tissues far from bony structures seen on x-ray film. A marker embedded in the deeper part of the canal adds a new level of precision to all measurements involving this part of the head.

3. This method places a deep x-ray marker 60 in the more stable part of the canal 61, where it will be closer to rigid bone and least affected by placement of the earpost socket or by the degree of insertion of the earposts for each x-ray exposure.

Figure 3A:
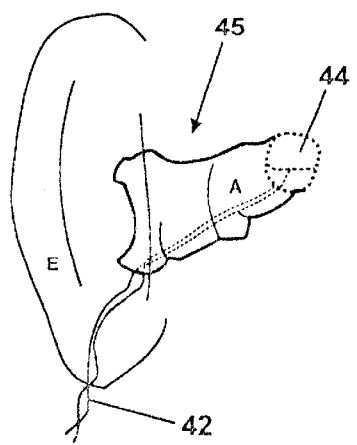
FIG. 3a is a schematic posterior elevation view illustrating the external ear in transparent outline and the auditory canal with an earmold impression including a canal blocker inside the canal with an attached retrieval thread embedded in the earmold.
Figure 3B:
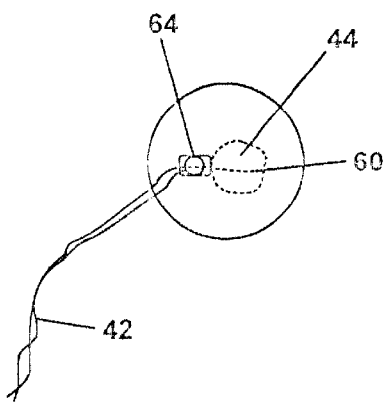
FIG. 3b is a schematic view of the blocker illustrated in FIG. 3a with a retrieval thread and also illustrating a radiopaque marker attached by activated shrinkable tubing ready for placement in the ear.
Figure 3C:
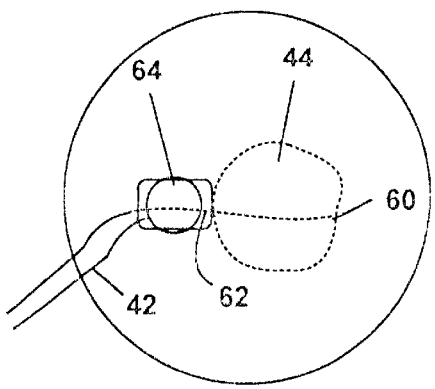
FIG. 3c is a schematic enlarged view of FIG. 3b.
Figure 4A:
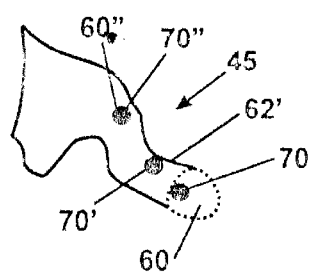
FIG. 4a is a schematic illustration of radiopaque markers embedded in three different positions in a finished earmold.
Figure 4B:
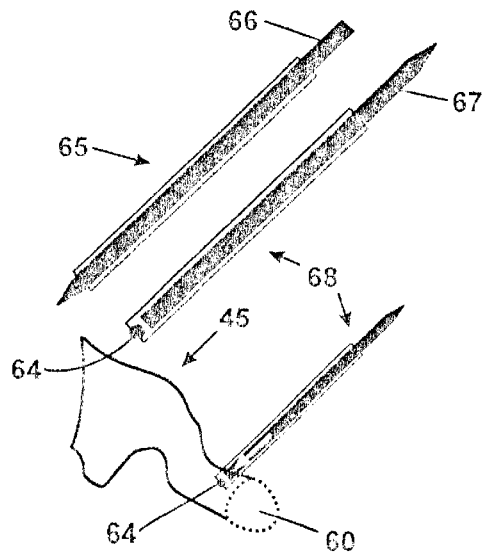
FIG. 4b is a schematic illustration of insertion of a marker in an earmold using a carrier and insertion device.

A radiopaque marker 60 such as a lead shot or other small metal shape is securely embedded or otherwise securely attached to the impression in the desired location in the ear canal 10. Two methods for secure attachment (FIGS. 3 and 4) are:

A. One method is to attach the marker 60 to the retrieval thread 42 close to the impression blocker 44, as by inserting it in a small section of heat-shrinkable tubing 62 threaded onto the retrieval thread 42 near or inside of the blocker. The marker 60 is inserted into the tube 62 and secured by the application of heat to shrink the tubing onto blocker 44 and thread 42. Adhesives, including polymers, may also be used to provide secure attachment.

B. A second method provides more control over exact placement by inserting the marker 60 after the material has set and the finished earmold 45 removed from the ear. This requires a hole 70, 70' 70" and insertion of the marker 60, 60', 60" into the earmold 45 having a body portion 46. The hole and its preparation prior to placement of the marker depends on the physical properties of the material. A preferred method (FIG. 4b) uses a thin tube 65 with a slideable pointed insert 66 in the lumen, so that the combination provides a means for creating an opening 60, 60', 60" in the earmold for insertion of the marker. The insertion is accomplished by removing the insert 66 from the tube 65 while maintaining the open hole with the tube. The marker 60 inserted through the tube into the hole as by reversing as indicated at 68 and rieinserting the insert 67 to provide a blunt end. It is held in place in the hole by the insert while the tube is withdrawn before the insert.

4. The original impression 40 can function as the locator as described above, or it can be used for laboratory fabrication of a duplicate using methods and materials known to the art.

Both the integrated socket 56 and radiopaque marker 60 contribute greatly to the precision of measurement of the resulting x-ray images. Either may be used independently, but the combination is required for most applications.

Locators 50 fabricated by this method can be filed and re-used for successive procedures on the same patient, assuring the consistent orientation that is accurate serial comparisons or for fabrication of appliances and prostheses.

What is claimed is:

1. A method of making an ear canal locating device comprising:
   providing non-shrinking elastic material which is non-toxic to an ear canal and adopted to solidify at temperatures within a human ear canal;
   inserting means for defining an inner end of said device by blocking flow of said material when it is introduced into said canal;
   locating a radiopaque marker in said inner end before liquid is injected into said ear canal;
   liquefying said material;
   injecting said liquefied material into said ear canal;
   allowing said material to solidify within said ear canal to form an impression, and removing said impression after it has solidified in said ear canal.

2. A method according to claim 1 including locating a socket within said outer canal before said liquid solidifies in said ear canal.

3. An ear canal locating device comprising:
   an elastic earmold impression made of a material which is non-toxic to an ear canal and adapted to solidify at temperatures within a human ear canal having an external face comprising a socket having a flange portion and a body portion; said body portion having means thereon for increasing engagement of said socket with said impression.

4. A locating device according to claim 3 wherein said device is made from a material selected from the group consisting of acrylic material, polycarbonate material, and silicone rubber.

5. An ear canal locating device according to claim 3 wherein said socket is a radiolucent socket.

6. An ear canal locating device according to claim 5 wherein said means for increasing engagement of said socket with said impression comprise at least one protrusion.

7. An ear canal locating device according to claim 5 wherein said means for increasing engagement of said socket with said impression comprise at least one ring.

8. An ear canal locating device according to claim 3 wherein said impression contains a radiopaque marker.

9. An ear canal locating device according to claim 8 wherein said radiopaque marker is located within a shrinkable enclosure.

10. An ear canal locating device according to claim 9 wherein said locating device includes blocking means for blocking penetration of said impression into said ear canal.

11. An ear canal locating device according to claim 10 wherein said locating device includes blocking removing means for removing said blocking means from said ear canal.

12. An ear canal locating device according to claim 11 wherein said locating device includes marker removing means for removing said marker and shrinkable enclosure from said ear canal.

13. An ear canal locating device according to claim 11 wherein said blocking removing means comprises a flexible cord.

14. An ear canal locating device comprising:
   an elastic earmold impression made of a material which is non-toxic to an ear canal and adapted to solidify at temperatures within a human ear canal having an external face comprising a socket having a flange portion and a body portion;
   said locating device containing a radiopaque marker;
   said locating device including blocking means for blocking penetration of said impression into said ear canal;
   said locating device including blocking removing means for removing said blocking means from said ear canal.

15. An ear canal locating device according to claim 14 wherein said body portion includes engagement means thereon for increasing engagement of said socket with said impression.

16. An ear canal locating device according to claim 15 wherein said means for increasing engagement of said socket with said impression comprise at least one protrusion.

17. An ear canal locating device according to claim 15 wherein said engagement means for increasing engagement of said socket with said impression comprise at least one ring.

18. An ear canal locating device according to claim 14 wherein said radiopaque marker is located within a shrinkable enclosure.

19. An ear canal locating device according to claim 18 wherein said locating device includes marker removing means for removing said shrinkable enclosure from said ear canal.

20. An ear canal locating device according to claim 19 wherein said marker and said impression comprise a unit remaining in the ear canal.

21. An ear canal locating device according to claim 14 wherein said removing means comprises a flexible cord.

22. An ear canal locating device according to claim 14 wherein at least one hole is provided in said device for said radiomarker.

23. An earmold comprising:
   an elastic earmold impression made of a material which is non-toxic to an ear canal and adapted to solidify at temperatures within a human ear canal having an external face having a flange portion adapted to engage an external portion of an ear; and a body portion adapted to extend deep within said ear canal, said body portion having an inner end; and said impression containing a radiopaque marker within said inner end.

24. An earmold according to claim 23 wherein at least one hole is provided in said inner end of said marker.

25. An earmold according to claim 24 wherein said earmold includes blocking means for blocking penetration of said impression into said ear canal.

26. An earmold according to claim 23 wherein said radiopaque marker is located within a shrinkable enclosure.

27. An earmold according to claim 26 wherein said earmold includes marker removing means for removing said marker and shrinkable enclosure from said ear canal.

28. An ear canal locating device according to claim 27 wherein said removing means comprises a flexible cord.

* * * * *